United States Patent [19]

Stutz

[11] Patent Number: 5,194,911
[45] Date of Patent: Mar. 16, 1993

[54] METHOD AND APPARATUS FOR DETERMINING THE QUANTITY OF MATERIAL TRANSPORTED WITHIN A FIBRE BAND OR SLIVER

[75] Inventor: Hansruedi Stutz, Dietlikon, Switzerland

[73] Assignee: Gebruder Loepfe AG, Kempten, Switzerland

[21] Appl. No.: 665,764

[22] Filed: Mar. 6, 1991

[30] Foreign Application Priority Data

Mar. 8, 1990 [CH] Switzerland ............. 741/90

[51] Int. Cl.[5] ............................. D01G 15/46
[52] U.S. Cl. ..................... 356/242; 19/0.23; 356/429
[58] Field of Search ........... 356/238, 242, 372, 429; 19/0.21, 0.23, 106 R, 150; 250/559, 571

[56] References Cited

U.S. PATENT DOCUMENTS

| | | | |
|---|---|---|---|
| 3,496,366 | 2/1970 | Hunziker et al. | 250/571 |
| 3,684,378 | 8/1972 | Lord | 356/434 |
| 4,962,569 | 10/1990 | Hösel | 19/0.23 |

FOREIGN PATENT DOCUMENTS

| | | |
|---|---|---|
| 1510325 | 3/1970 | Fed. Rep. of Germany ...... 356/242 |
| 274241 | 12/1989 | German Democratic Rep. . |
| 274242 | 12/1989 | German Democratic Rep. . |

Primary Examiner—Richard A. Rosenberger
Attorney, Agent, or Firm—Harness, Dickey & Pierce

[57] ABSTRACT

A fibre band or sliver is passed through a defined opening of a measuring station. Said opening has a cross section smaller than the diameter of the fibre band, so that the band contacts the walls of said opening which thereby defines a measuring cross section. The fibre band while passing said opening is transilluminated by at least one light source. The transmitted light intensity is measured by a light receiver and is detected as a measure for the quantity of the fibre material present in said cross section.

7 Claims, 3 Drawing Sheets

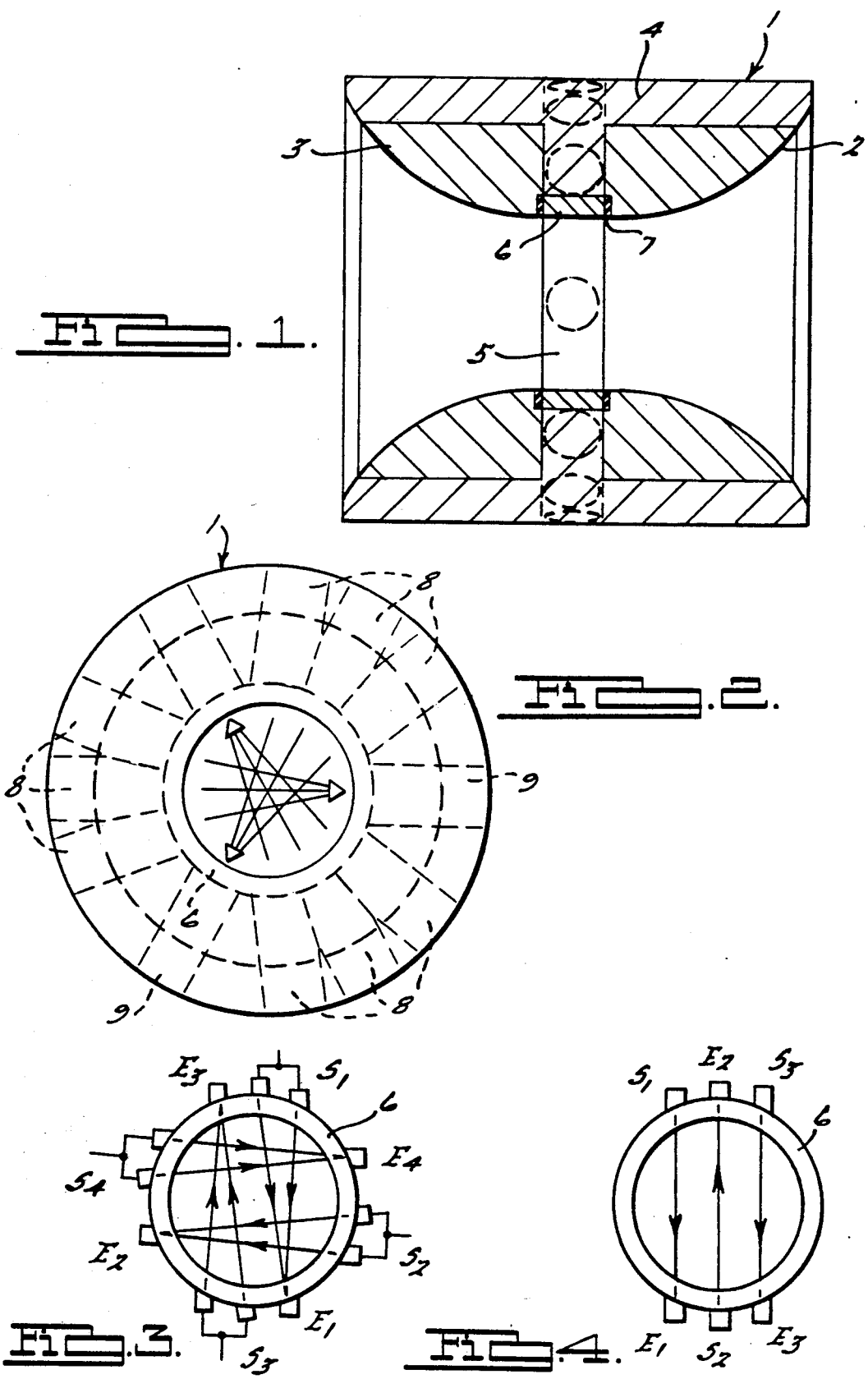

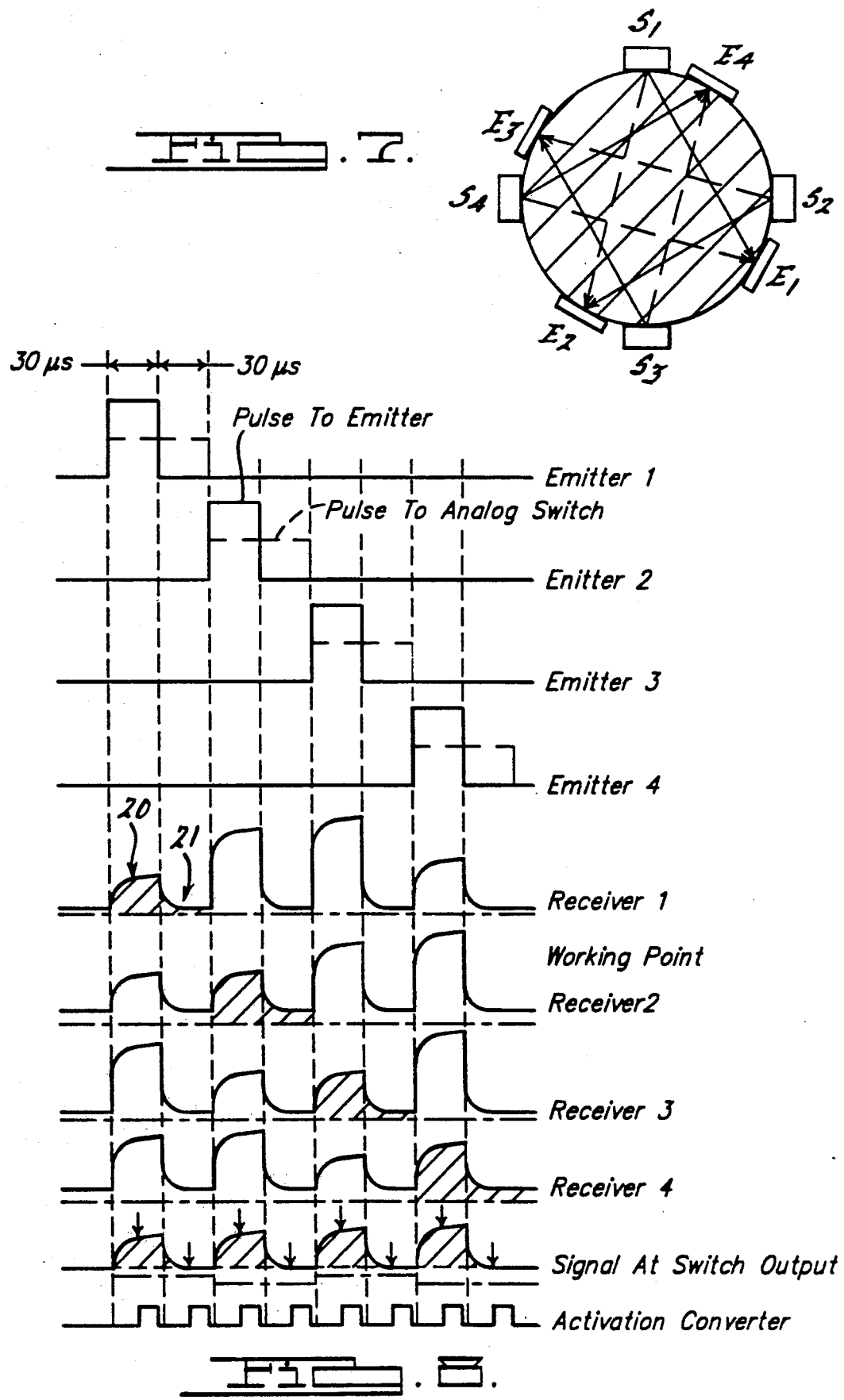

METHOD AND APPARATUS FOR DETERMINING THE QUANTITY OF MATERIAL TRANSPORTED WITHIN A FIBRE BAND OR SLIVER

BACKGROUND OF THE INVENTION

The invention refers to a method and apparatus for continuously measuring the quantity of fibre material transported within a fibre band, as e.g. in card sliver or a drafter sliver in textile industry. The measuring results are used for the control of the carding machine or the drafter producing the sliver. Several measuring principles were used for such measurement in the past which will be described first.

DESCRIPTION OF THE PRIOR ART

A first known measuring principle is based on the capacity test, wherein the textile fibre band is passed between two condenser plates. The capacity measured between these plates depends not only on the actual quantity of fibre material present between the plates but also on the specific inductive capacity of the material, the temperature and the water content. Though by this method the sliver is not mechanically loaded, it is disadvantageous because it is critical to static electricity of the material and is dependent on the humidity and the quality of the material to be measured.

Another measuring principle is based on mechanical sensing of the sliver by means of a pair of displaceable rollers, between which the sliver is passed. The actual distance between the rollers then is equivalent to the quantity of material between the rollers. Though this method is independent of the type and the properties of the material and results in stable absolute measuring values for the quantity of material in the sliver, it has the disadvantage of additionally loading the sliver by pressing it and by acting frictional forces on it.

Finally, a third known measuring method is based on pneumatical measurement. The sliver is passed through a trumpet-shaped, narrow opening having a transverse bore at its narrowest point. In this bore an overpressure is generated when the sliver is passed through said opening, because the air within the sliver is compressed. By this method the sliver is not excessively loaded, but the measuring results strongly depend on the transporting speed of the sliver and on the type of fibre material. Moreover, it is sensitive to collecting dirt and difficult to be calibrated and the length of the measuring zone is longer than 5 mm.

As can be seen from the above description of the prior art, each of the known methods has specific disadvantages because the sliver is loaded or the measuring results are influenced by the type and the properties of the material.

SUMMARY OF THE INVENTION

Hence, it is a general object of the present invention to provide a new method and apparatus for a continuous measurement of the quantity of fibre material transported in a fibre band or sliver which independently of the above mentioned influences allows to achieve stable measuring values proportional to the quantity of material in the sliver without causing excessive mechanical load on the same.

A further object of the invention is to provide a new measuring method and apparatus for the quantity of fibre material in a sliver which is self-cleaning and therefore needs substantially no maintenance.

Still a further object of the invention is to provide a new measuring method and apparatus, wherein the influence of local fibre accumulations within the sliver can be considered by multiple measurements for each cross section of the sliver and by taking the mean of the measured values.

Finally, it is an object of the invention to provide a new measuring method and apparatus for the control of carding machines or drafters dependent of the measured quantity of fibre material in the sliver in textile plants.

Now, in order to implement these and still further objects of the invention, which will become more readily apparent as the description proceeds, the new method is manifested by the features that the fibre band or sliver is passed through a defined opening of a measuring station, said opening having walls which are contacted by the surface of the fibre band to define a measuring cross section of the fibre band to which the fibre band is compressed, and that the fibre band while passing through said opening is transilluminated by at least a light source from said wall, wherein the transmitted light intensity is received by at least a light receiver and is detected as a measure for the quantity of fibre material present in said cross section of said opening. Preferably, said wall is formed by a ring of transparent material, through which the light is emitted immediately into the fibre band which contacts the surface of the transparent ring and through which the transmitted light is detected.

By this method and arrangement the position and the cross section of the fibre band or sliver is exactly and reproducibly defined at the measuring station, so that the geometrical conditions for the measurement remain always the same and the influence of stray light can be eliminated. Because the fibre band always contacts the inner surface of the transparent ring when passing therethrough, the optic measurement is not affected by any dirt deposition. Under these conditions the amount of light transmitted through the fibre band is almost exactly inversely proportional to the total mass of the fibres present in the measuring cross section. However, for considering that fact that the distribution of fibres is not equal over the whole cross section because local fibre concentrations may be present, the transillumination measurement of the fibre band is done simultaneously along several paths distributed over the cross section. By taking the mean value from these measurements for each measured cross section of the fibre band as a measure for the fibre quentity the fluctuation of the measured values can be reduced.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 is a longitudinal sectional view of the measuring station of the invention;

FIG. 2 is an axial view onto the opening of the measuring station with indicated paths of light transmission;

FIG. 3 is a schematic axial view of the measuring station showing a first possible arrangement of light emitters and light receivers and respective light transmission paths;

FIG. 4 is a second possible arrangement of light emitters and light receivers;

FIG. 7 is a schematic view of a third possible arrangement of the light emitters and the light receivers corresponding to the block diagram of FIG. 6, and FIG. 8 is a timing diagram of the signals of the light emitters and receivers corresponding to FIGS. 6 and 7.

DESCRIPTION OF THE PREFERRED EMBODIMENTS

Figure 5:
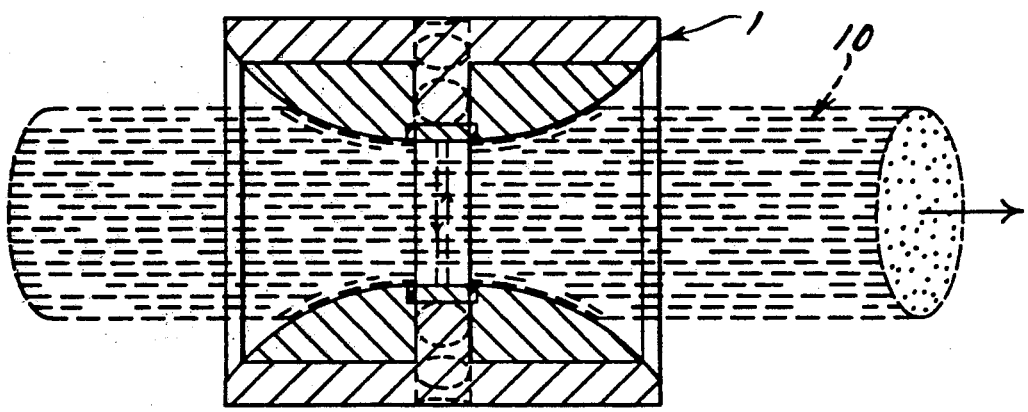
FIG. 5 is a longitudinal sectional view of the measuring station with a fibre band present in the opening.

In FIGS. 1 and 2 a measuring station 1 is exhibited without showing the optical elements which will be explained later on. The station 1 comprises a funnel shaped inlet opening 2 and a funnel shaped outlet opening 3 for the fibre band or sliver. The inlet and outlet openings are formed as inserts 2, 3 supported within a tubelike casing 4. The inlet 2 is narrowing conically to a minimum cross section 5 which is the measuring cross section. In this zone light emitters $S_1$, $S_2$, ... and light receivers $E_1$, $E_2$, ... are placed behind a transparent ring 6, as can be seen from the FIGS. 3, 4 and 7. The transparent ring 6 preferably is made of glass which is transparent for infrared light, as e.g. Pyrex glass. It has a relatively thin wall of about 1 mm to avoid excessive light absorption or light conduction in the ring. Its inner diameter is adapted to the diameter of the fibre band or sliver to be measured so that the surface of the fibre band contacts the inner wall of the glass ring 6 on all sides. The fibre band thereby is compressed only slightly, as can be seen from FIG. 5. FIGS. 1, 2 and 5 are enlarged views of the measuring station, which in reality may have a minimum inner diameter of e.g. 10 mm depending on the sliver to be measured.

The glass ring 6 is supported in the casing 4 and sealed by means of sealings 7 towards the inserts 2 and 3 to avoid any entrance of dust from the sliver into the space behind the glass ring 6. The inner wall of the ring 6 in operation is cleaned by the sliver itself passing therethrough, so that constant optical conditions are maintained.

In FIG. 2 the measuring station 1 is shown in an axial view along the axis of the fibre band to be measured. The radial dotted lines indicate radial bores 8 for light emitters S and radial bores 9 for light receivers. The geometrical arrangement of the light transmitters and receivers will be discussed in detail in connection with the description of the FIGS. 3, 4 and 7.

The light emitters $S_1$, $S_2$, ... preferably are infrared light emitting diodes (GaAlAs - diodes) which in pulsed operation have a high light efficiency (10 mW to 300 mW) and have a forwardly directed emission pattern. The light emitters $S_1$, $S_2$, ... are distributed over the circumference of the glass ring 6 defining several light transmission paths through the fibre band distributed over its cross section. Substantially opposite to the light emitters $S_1$, $S_2$, ..., there are light receivers $E_1$, $E_2$, ... arranged behind the glass ring 6, for which photoelectric diodes (pin-diodes) are used. Between the light emitters $S_1$, $S_2$, ... and the corresponding light receivers $E_1$, $E_2$, ... light transmission paths are defined, along which the measurements are carried out. As will be explained in more detail later one, the measuring result is gained by taking the mean value of the measurements along the plurality of transmission paths. Thereby, unequal fibre distributions over the measured cross section do not affect the measurement.

In FIG. 3 an embodiment is exhibited, wherein for each transmission path two light emitters cooperate with one light receiver so that the light intensity in each path is doubled. The arrangement shown in FIG. 2 equally is designed for three light emitters cooperating with each light receiver, as can be seen from the groups of three bores 8 (for the light emitters) opposite to each bore 9 (for the light receiver). Thereby, the light intensity can be tripled. Returning to FIG. 3, it can be seen that there are pairs of substantially parallel transmission paths. However, the directions of light transmission on these paths are opposite to each other. Thereby, crosstalking between adjacent transmission path can be avoided, in that each receiver only receives light emitted by the corresponding light emitter(s). The same is true for the arrangement of FIG. 4, where the transmission paths all extend in one direction.

As can be seen from the described arrangements of the light emitters and receivers, the transmission paths form a kind of lattice-structure in the narrow measuring zone within the glass ring 6, thereby covering substantially the whole cross section of the fibre band to be measured.

In FIG. 5 the position of the fibre band 10 when passing through the measuring station 1 is shown. During the measurements the fibre band or sliver 10 is moved through the measuring station 1 with a velocity of e.g. 600 m/min. Since the quantity of material in the fibre band is to be determined permanently, the intervals between two subsequent measuring cycles must not be too large. In the embodiment described each 4 mm in longitudinal direction of the band 10 a measuring cycle is carried out.

Figure 6:
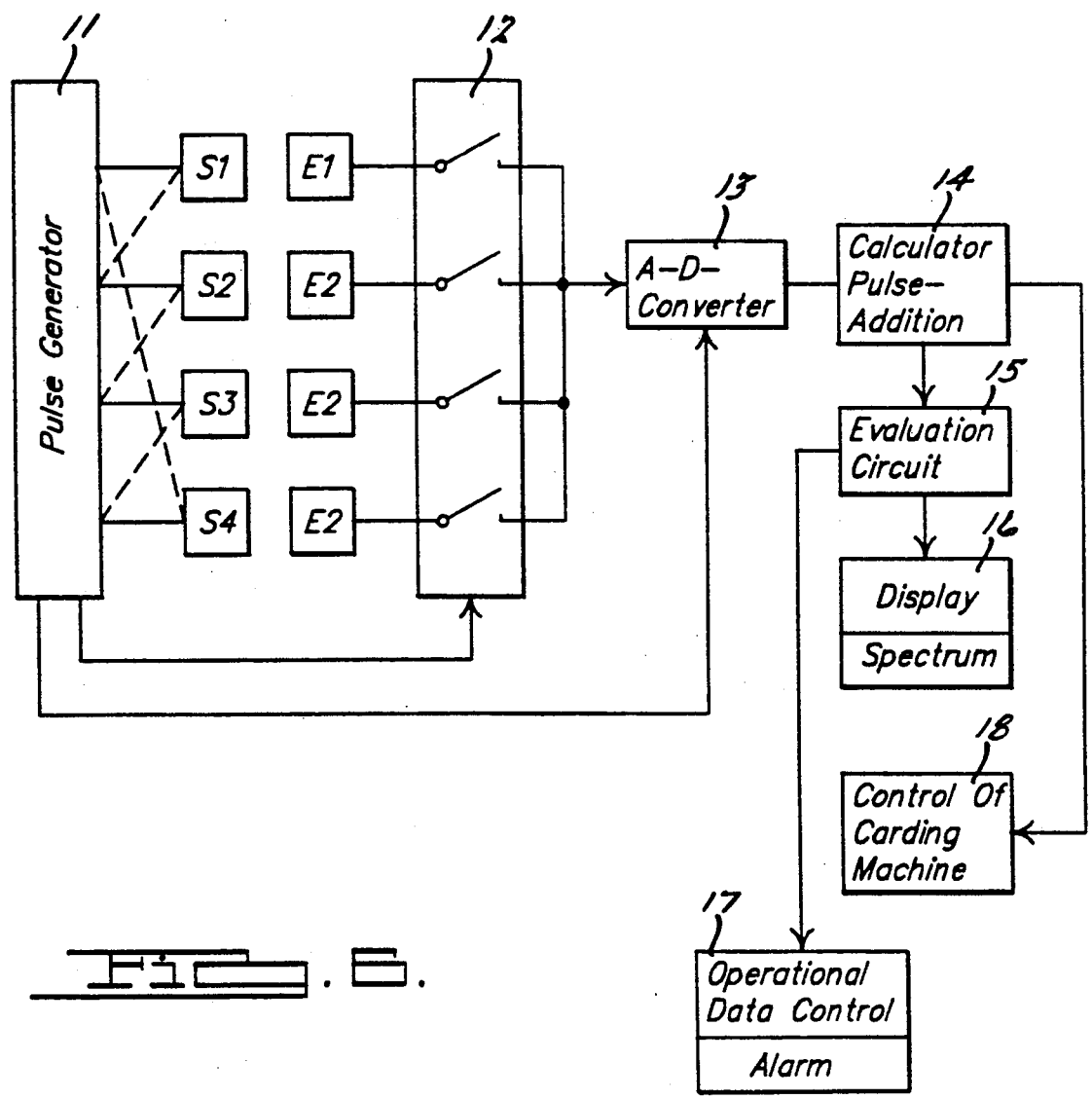
FIG. 6 is a block diagram of an evaluation circuit.

A necessary condition for that is to have quick electronic circuits and microprocessors for the evaluation of the data. In FIG. 6 a configuration of such electronic circuits is shown.

In a pulse generator circuit 11 current pulses having a length of about 30 μsec are generated and are subsequently supplied to one of the light emitters $S_1$ to $S_4$. The pulses simultaneously are used for controlling an analog switch 12 connected between each receiver $E_1$ to $E_4$ and an analog-to-digital converter 13. The analog switch 12 is controlled to subsequently connect each receiver $E_1$ to $E_4$ one after another to the A/D-converter 13. Thereby, a correlation of time between defined transmitters and defined receivers is achieved, so that the signal received in the receiver $E_1$ e.g. exactly corresponds to the light transmitted along the path between the emitter $S_1$ and the receiver $E_1$ (see FIGS. 7 and 8). The analog switch 12 is closed for an interval which not only corresponds to the mentioned current pulse 20, but also includes a subsequent dark phase 21, as can be seen in FIG. 8. Thereby, in each receiver not only the light pulse is detected but also the signal level in the dark phase 21, which allows to determine a differential signal for each receiver which is independent of the working point of the same. The A/D-converter is controlled to be operated also during the dark phase, so that from each receiver a digital signal is received as indicated by the hatched signal portions in FIG. 8.

The first four lines of FIG. 8 exhibit the above mentioned current pulses and control signals, respectively, for each transmission path 1 to 4 during one measuring cycle. The fifth to eighth line in FIG. 8 show the signals received in the respective light receivers E1 to E4, of which only the hatched portion is evaluated which belongs to the light transmission from the corresponding light emitter. On the ninth line of FIG. 8 the signal at the output of the analog switch is shown which is composed of the subsequent signals from the receivers $E_1$ to $E_4$. On the last line the control signals for the activation of the A/D-converter 13 are shown. The corresponding digital values evaluated by the A/D-converter 13 are marked by means of arrows in the second to the last line of FIG. 8. As can be seen from this line, the difference between the signal received by each receiver E1 to E4 in a first "bright" interval and a subsequent "dark" interval is calculated in a calculation circuit 14, whereby the different working points of the receivers E1 to E2 indicated by dash dotted lines in the diagram of FIG. 8 can be compensated.

The complete measuring cycle for one measurement as shown in FIG. 8 lasts about 240 μsec including four subsequent transmission measurements along four transmission paths. In the calculation circuit 14 the four digital signals from the four transmission paths (i.e. the differential values as explained above) are added. Such addition is mathematically equivalent to taking the mean value of the four measurements and results in an elimination of the influence of unequal fibre distribution in the measured cross section.

In an evaluation circuit 15 having a data storage the measuring results are stored and processed for being displayed on a display unit 16 and recorded in an operating conditions control system 17. Furthermore, the data from the calculation circuit 14 can be used in a control circuit 18 for controlling the drafter or the card by which the band is produced. Such control circuits 18 are known to the man skilled in the art and therefore do not need to be described in detail.

The measurements as described above are carried out in succession. If one measuring cycle needs a total of about 250 μsec, 2500 measurements can be done in each second. Since in one second the fibre band is moved over a distance of about 10 m, each measurement corresponds to a length of 4 mm of the band. Thereby, a practically continuous measurement of the fibre quantity in the fibre band or sliver is achieved.

The measuring station 1 is structured to act only a minimal load upon the fibre band, in that it is only slightly compressed as necessary to contact the inner wall of the glass ring 6. Since the measuring results are obtained optically, they are not influenced by the velocity, the temperature, the humidity or electrostatic properties of the fibre band. The measuring station is self-cleaning because any dust deposition in the optical path is avoided by the moving fibre band itself.

As explained, the light intensity value measured in the light receivers is evaluated to consider the difference between the intensity measured during the emission of a light pulse and the intensity measured during a subsequent "dark" interval in the result. Therefore, this result is an absolute, inverse measure for the quantity of fibre material present in the cross section of the measuring station during the measuring cycle. Any drift of the working points of the light receivers thereby is eliminated by the measuring procedure itself and does not influence the results.

While there are shown and described present preferred embodiments of the invention, it is to be distinctly understood that the invention is not limited thereto, but may be otherwise variously embodied and practiced within the scope of the following claims.

I claim:

1. A method for determining the quantity of fibre material transported in a fibre band or sliver, wherein the fibre band or sliver is passed through an opening of a measuring station defined by walls, said opening having a cross section smaller than a diameter of the fibre band or sliver so that it contacts said walls of the opening which thereby defines a measuring cross section, wherein the fibre band while passing said opening is transilluminated between said walls by means of a plurality of light emitters and a plurality of light receivers arranged at said opening and operated so that each transmitted light intensity value received by a light receiver corresponds to a defined path of the light through said measuring cross section, wherein a plurality of such defined light paths is provided between said light emitters and said light receivers, said paths being distributed over said measuring cross section, wherein the light emitters and/or light receivers during a measuring cycle are operated sequentially so that the transmitted light intensity values along each of said plurality of paths are measured successively during a measuring cycle, and wherein during a measuring cycle a mean value or added value of the light intensity values received by said light receivers is formed as a measured for the quantity of fibre material present in said measuring cross section during the measuring cycle.

2. The method of claim 1, wherein the plurality of light emitters during a measuring cycle is operated to emit light pulses successively one after another, and wherein the corresponding light receivers are connected successively one after another to an evaluation circuit in correspondence to said defined light paths.

3. The method of claim 2, wherein for each light receiver a transmitted light intensity signal is detected during the light pulse of the corresponding light emitter and also during a subsequent dark interval, in which no light pulse is emitted, and wherein the difference value of said two detected signals is evaluated as a measuring value of the respective light receiver.

4. Apparatus for determining the quantity of fibre material transported in a fibre band or sliver comprising a measuring station defining an opening, through which the fibre band or sliver is passed, said opening having a cross section which is smaller than across section of said fibre band or sliver to be measured, said measuring station being provided with a plurality of light emitters and a plurality of light receivers arranged at said opening and connected to said evaluation circuit such tat each light receiver is associated to at least one defined light emitter, whereby a plurality of defined light paths are defined through said opening between said light emitters and said light receivers, said light paths being distributed over the cross section of said opening;

comprising an evaluation circuit connected to said light receivers, aid light receivers being arranged to measure at least an intensity value of light transmitted through said fibre band or sliver along said light path, said measured intensity value being supplied to said evaluation circuit for determining therefrom the quantity of fibre material present in said opening;

and comprising a pulse generator connected to said light emitter for successively activating the light emitters to emit light pulses one after another, wherein said evaluation circuit is connected to said light receivers via a controlled switch for selectively connecting the light receiver associated with the activated light emitter to said evaluation circuit.

5. Apparatus of claim 4, wherein said measuring station is provided with an inlet funnel for the fibre band or sliver, which inlet funnel is conically narrowing from a diameter larger than a diameter of the fibre band or sliver said opening.

6. Apparatus of claim 4, wherein said at least one light emitter is at least one infrared light emitting diode arranged in a casing of said measuring station at said opening.

7. The apparatus of claim 4, wherein said opening is formed by a ring of at least partially transparent material, and wherein said light emitters and said light receivers are arranged behind said ring at said opening.

* * * * *